(12) United States Patent
Zhang et al.

(10) Patent No.: US 7,649,120 B2
(45) Date of Patent: Jan. 19, 2010

(54) MICROWAVE-ASSISTED EXTRACTION OF SOLANESOL FROM POTATO STEMS AND/OR LEAVES

(75) Inventors: Ji Zhang, Lanzhou (CN); Xiaolong Xu, Lanzhou (CN); Tong Chen, Lanzhou (CN); Junyi Ma, Lanzhou (CN); Jian Yao, Lanzhou (CN); Junyu Liang, Lanzhou (CN); Yunpu Wang, Lanzhou (CN); Junlong Wang, Lanzhou (CN); Guoxue Liu, Lanzhou (CN)

(73) Assignee: Northwest Normal University, Gangsu (CN)

( * ) Notice: Subject to any disclaimer, the term of this patent is extended or adjusted under 35 U.S.C. 154(b) by 0 days.

(21) Appl. No.: 12/372,924

(22) Filed: Feb. 18, 2009

(65) Prior Publication Data

US 2009/0209789 A1    Aug. 20, 2009

(30) Foreign Application Priority Data

Feb. 20, 2008    (CN)    ........................ 2008 1 0057908

(51) Int. Cl.
  *C07C 33/02* (2006.01)
(52) U.S. Cl. .................. 568/875; 568/868; 204/157.67; 204/157.9
(58) Field of Classification Search ................ 568/868, 568/875; 204/157.67, 157.9
  See application file for complete search history.

(56) References Cited

FOREIGN PATENT DOCUMENTS

| CN | 91103632.6 | 11/1991 |
|---|---|---|
| CN | 93106316.7 | 5/1994 |
| CN | 93118734.6 | 11/1994 |
| CN | 94102575.6 | 9/1995 |
| CN | 94107849.3 | 1/1996 |
| CN | 94115570.6 | 3/1996 |
| CN | 99117334.1 | 5/2001 |
| CN | 00123921.X | 4/2002 |
| CN | 02134560.0 | 2/2003 |
| CN | 01108703.X | 3/2003 |
| CN | 200410013561.1 | 10/2004 |
| CN | 200410040400.1 | 6/2005 |
| CN | 200410053681.4 | 6/2005 |
| CN | 200510042787.9 | 12/2005 |
| CN | 200510094288.4 | 4/2006 |
| CN | 200510124541.6 | 7/2006 |

*Primary Examiner*—Elvis O Price
(74) *Attorney, Agent, or Firm*—Scully, Scott, Murphy & Presser, P.C.

(57) ABSTRACT

This invention relates to a method of extracting solanesol by microwave-assisted from potato stems and/or leaves. In particular, the invention provides a technique whereby the solanesol can be extracted effectively, in a relatively short period of time with respect to conventional extraction methods and allows for an enhanced extraction yield. The invention has bright perspectives in promoting local economic development and increasing farmers' income.

1 Claim, 2 Drawing Sheets

MICROWAVE-ASSISTED EXTRACTION OF SOLANESOL FROM POTATO STEMS AND/OR LEAVES

BACKGROUND OF THE INVENTION

1. Technical Field

This invention relates to a method of extracting solanesol. In particular, the invention provides a technique whereby the crude solanesol can be extracted by microwave-assisted from potato stems and/or leaves.

2. Background

Solanesol, a long-chain terpenoid alcohol, is the starting material for many high-value biochemicals, including Vitamin K analogues and co-enzyme Q10 which is useful in the treatment of heart diseases, cancers and ulcers. Co-enzyme Q10 is widely used in medicine field, health care field and cosmetic area. It present in virtually in every cell in the human body and is known as the "miracle nutrient". It can be also used as anti-aging, treatment senile dementia and congenital anemia.

China patent CN 91103632.6 and CN 93118734.6 describe an extraction method of solanesol from discarded or moldy tobacco leaves. China patent CN 93118734.6 reports a preparation method of unsaponified solanesol. China patent CN 94102575.6 describes an extraction method and equipment of solanesol. China patent CN 94115570.6 reports a process for producing solanesol. China patent CN 99117334.1 describes a process for extracting solanesol. China patent CN 02134560.0 describes a solanesol complex and process for producing the same. China patent 200410013561.1 provides a process for extracting and purifying solanesol from potato leaves. A deep processing of tobacco concrete for producing tobacco absolute and solanesol: see China patent CN 01108703.X. China patent 200410053681.4 provides a process for clean preparation of high-purity solanesol. China patent 200410040400.1 describes a high-purity solanesol and synthesize for producing the same. Solanesol is extracted from potato leaves and then purifying the solanesol by crystallizing from an organic solvent. The purity of solanesol is higher than 90%, e.g. China patent CN 1762940A describes a process for extracting and purifying solanesol from potato and potato leaves, with organic solvent extraction and recrystallization, the purity of solanesol is higher than 90%.

There is large planting area of potato in Chinese rural. The yield of potato is almost 3 million tons in Dingxi area, Gansu province. However, about 550 thousands ton of potato leaves are not effectively utilized. There would be 1.375 thousands ton of solanesol if half of the leaves were used. The economic benefit is notable.

The most conventional method for extraction of solanesol from potato leaves is heat-reflux extraction with an organic solvent in which the solanesol is soluble. The disadvantages of the method are: time-consuming, high consumption of solvent, higher energy consumption and high cost.

Microwave energy penetrates materials and produces a volumetrically distributed heat source due to molecular friction resulting from dipolar rotation of polar solvents and from the conductive migration of dissolved ions. The highly localized temperature and pressure can cause selective migration of target compounds from the material to the extraction solvent at a more rapid rate and with similar or better recoveries compared with conventional heat-flux extraction.

So far, no literatures or patents refer to microwave-assistant extraction of solanesol from potato stems and/or leaves.

SUMMARY

The invention relates to a process for the manufacture of solanesol with microwave-assistant from potato stems and/or leaves. In accordance with the invention, an extraction protocol for solanesol can be performed when a microwave applicator is used to generate a sudden temperature increase inside of the potato leaves, e.g. the gland system of plant material, that is contacted with an appropriate quantity of a selected extraction medium that is (a) transparent to microwave so as to keep the environment that surrounds the material cold with respect to the internal temperature of the material itself, or (b) partially transparent where some warming is permissible or desirable. Compared with conventional methods, the invention can considerably reduce both extraction time and energy consumption. It also has bright perspectives in promoting local economic development and increasing farmers' income.

The invention relates to a fast and efficient process for the manufacture of solanesol with microwave-assistance from potato stems and/or leaves.

The main objective of the invention is to provide a microwave-assistance process for the preparation of solanesol from potato stems and/or leaves.

The first step: Fresh potato stems and/or leaves were dried under ambient temperatures and milled to 40 mesh powders by a mortar (selected by sieve), and then were kept at ambient temperature. Then, potato stems and/or leaves was mixed with ethanol (95%). The ratio of the mixture was 1:1 (w/w). The suspension was irradiated automatically with microwaves in a microwave-drying equipment (the temperature was about 30-40° C. with the pressure of 0.08 MPa for 10-20 min). The microwave irradiation power was 1000-1500 W, and a frequency of 2450 MHz, get material A.

The second step: Material A was immersed in ethanol (95%). The ratio of material A to ethanol (w/w) may range from 1:5 to 1:15. The suspension was irradiated with microwaves in microwave extraction equipment with water condenser. The overall microwave power was 1000 W-1500 W with the frequency of 2450 MHz. The suspension was exposed at microwave irradiation for 30-50 min at the temperature of 45-65° C., stirred at 60-100 rpm. The extraction product may be recovered from the extractant (after separation from the solids material as filtering at the pressure of 0.08 MPa). Ethanol was evaporated off from the resulting organic solvent extract at the temperature of 50° C., 0.08 MPa, get material B.

The third step: Material B was dried in microwave-drying equipment (at the temperature of 50° C., 0.08 MPa) for 10-12 hours. The overall microwave power was 1000 W-1500 W with the frequency of 2450 MHz, get crude solanesol with the content about 10%.

The Dionex Ultimate 3000 high performance liquid chromatography (HPLC) system was equipped with a quaternary pump, an on-line solvent vacuum degasser and an auto sampler with a 20 ul injection loop. The detector was UV detector. The data were acquired and processed by means of Chromatography Management System. An Acclaim® 120 C18 column (150 mm×4.6 mm I.D., 4.5 um) fitted with a Jiajie C18 guard column (8 mm×4.6 mm I.D., 4.5 um) was used. The column temperature was set at 30° C. The mobile phase was chosen as methanol: ethanol (45:55, v/v) at a flow rate of 1 ml/min. The wavelength of UV detector was 211 nm.

This invention relates to a novel method of extracting crude solanesol from potato stems and/or leaves using microwave equipment as energy source. In particular, the invention provides a technique whereby the solanesol can be extracted effectively, in a relatively short period of time (30-50 min) with respect to conventional extraction methods (12-18 h) and allows for an enhanced extraction yield (about 10%). The drying of the extracts was decreased to 10-12 h compared with conventional method (36-48 h) use microwave-assistant drying equipment. Furthermore, the invention also allows for the extraction of material with less solvent consumption, energy conservation and environmental protection, and showed great potential for efficient sample preparation and large-scale industrial application in the near future. The invention has bright perspectives in promoting local economic development and increasing farmers' income.

DESCRIPTION OF DRAWINGS

Having thus generally described the invention illustrated a preferred embodiment.

DETAILED DESCRIPTION

Figure 1:
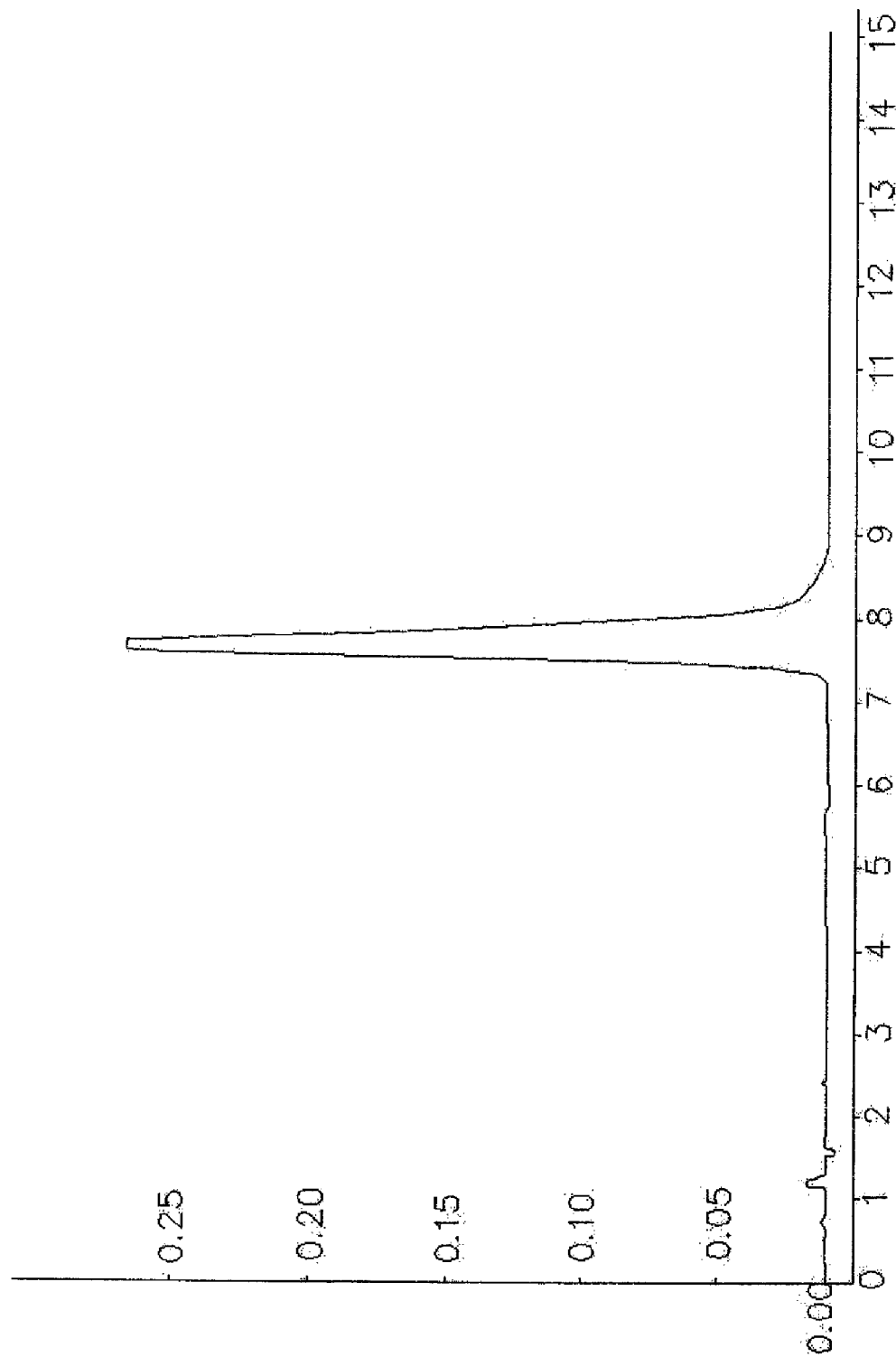
FIG. 1. The chromatogram of standard solanesol (200 ppm).
Figure 2:
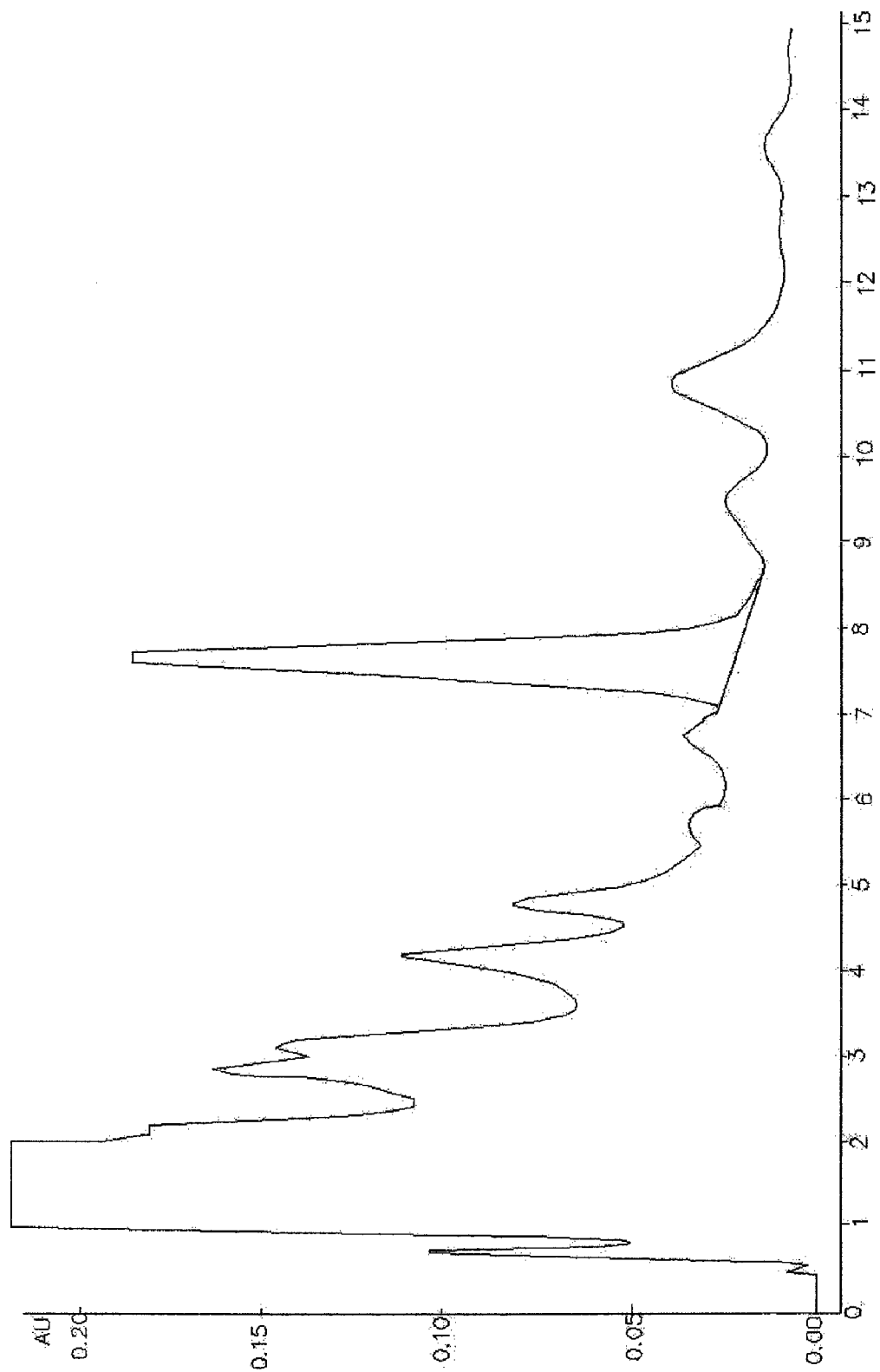
FIG. 2. The chromatogram of solanesol in the invention.

The following examples will illustrate the invention but the invention is not restricted to these examples.

EXAMPLE 1

The first step: Fresh potato stems and/or leaves were dried under ambient temperatures and milled to 40 mesh powders by a mortar (selected by sieve), and then were kept at ambient temperature. Then, potato stems and/or leaves was mixed with ethanol (95%). The ratio of the mixture was 1:1 (w/w). The suspension was irradiated automatically with microwaves in a microwave-drying equipment (the temperature was 35° C. with the pressure of 0.08 MPa for 15 min). The microwave irradiation power was 1100 W, and a frequency of 2450 MHz, get material A.

The second step: Material A was immersed in ethanol (95%). The ratio of material A to ethanol (w/w) may range from 1:8. The suspension was irradiated with microwaves in microwave extraction equipment with water condenser. The overall microwave power was 1200 W with the frequency of 2450 MHz. The suspension was exposed at microwave irradiation for 50 min at the temperature of 55° C., stirred at 80 rpm. The extraction product may be recovered from the extractant (after separation from the solids material as filtering at the pressure of 0.08 MPa). Ethanol was evaporated off from the resulting organic solvent extract at the temperature of 50° C., 0.08 MPa, get material B.

The third step: Material B was dried in microwave-drying equipment (at the temperature of 50° C., 0.08 MPa) for 12 hours. The overall microwave power was 1000 W with the frequency of 2450 MHz, get crude solanesol with the content about 10.8%.

EXAMPLE 2

The first step: Fresh potato stems and/or leaves were dried under ambient temperature and milled to 40 mesh powders by a mortar (selected by sieve), and then were kept at ambient temperatures. Then, potato stems and/or leaves was mixed with ethanol (95%). The ratio of the mixture was 1:1 (w/w). The suspension was irradiated automatically with microwaves in a microwave-drying equipment (the temperature was about 40° C. with the pressure of 0.08 MPa for 20 min). The microwave irradiation power was 1000 W, and a frequency of 2450 MHz, get material A.

The second step: Material A was immersed in ethanol (95%). The ratio of material A to ethanol (w/w) may range from 1:15. The suspension was irradiated with microwaves in microwave extraction equipment with water condenser. The overall microwave power was 1000 W with the frequency of 2450 MHz. The suspension was exposed at microwave irradiation for 40 min at the temperature of 65° C., stirred at 60 rpm. The extraction product may be recovered from the extractant (after separation from the solids material as filtering at the pressure of 0.08 MPa). Ethanol was evaporated off from the resulting organic solvent extract at the temperature of 50° C., 0.08 MPa, get material B.

The third step: Material B was dried in microwave-drying equipment (at the temperature of 45° C., 0.08 MPa) for 10 hours. The overall microwave power was 1500 W with the frequency of 2450 MHz, get crude solanesol with the content about 10.5%.

EXAMPLE 3

The first step: Fresh potato stems and/or leaves were dried under ambient temperature and milled to 40 mesh powders by a mortar (selected by sieve), and then were kept at ambient temperatures. Then, potato stems and/or leaves was mixed with ethanol (95%). The ratio of the mixture was 1:1 (w/w). The suspension was irradiated automatically with microwaves in a microwave-drying equipment (the temperature was about 30° C. with the pressure of 0.08 MPa for 10 min). The microwave irradiation power was 1500 W, and a frequency of 2450 MHz, get material A.

The second step: Material A was immersed in ethanol (95%). The ratio of material A to ethanol (w/w) may range from 1:5 to 1:15. The suspension was irradiated with microwaves in microwave extraction equipment with water condenser. The overall microwave power was 11500 W with the frequency of 2450 MHz. The suspension was exposed at microwave irradiation for 30 min at the temperature of 45° C., stirred at 100 rpm. The extraction product may be recovered from the extractant (after separation from the solids material as filtering at the pressure of 0.08 MPa). Ethanol was evaporated off from the resulting organic solvent extract at the temperature of 50° C., 0.08 MPa, get material B.

The third step: Material B was dried in microwave-drying equipment (at the temperature of 48° C., 0.08 MPa) for 11 hours. The overall microwave power was 1200 W with the frequency of 2450 MHz, get crude solanesol with the content about 10%.

For comparative purposes, the solanesol was obtained by a 6-8 h heat-reflux extraction (ethanol was chosen as solvent) with yields of about 9% based on vacuum drying.

TABLE 1

Comparison between microwave-assistant extraction and heat-reflux extraction

| Experiment No. | Extraction Time (min) | Extraction temperature (° C.) | Yield of crude solanesol (%) | Content of solanesol (%) |
|---|---|---|---|---|
| microwave-assistant extraction | 30-50 | 45-65 | 5-5.5 | 10-11 |

TABLE 1-continued

Comparison between microwave-assistant extraction and heat-reflux extraction

| Experiment No. | Extraction Time (min) | Extraction temperature (° C.) | Yield of crude solanesol (%) | Content of solanesol (%) |
|---|---|---|---|---|
| heat-reflux extraction | 12-26 | 65 | 6 | 9 |

What is claimed is:

1. A process for producing solanesol from potato stems or leaves with microwave-assistance, comprising:
   a. drying fresh potato stem or leaves under ambient temperature; milling the dried leaves to 40 mesh powders; mixing the powders with 95% ethanol at the ratio of 1:1 (w/w); and irradiating the mixture with microwaves in a microwave-drying equipment at about 30-40° C. under the pressure of 0.08MPa for 10-20 min to obtain Material A, wherein the microwave irradiation power is 1000-1500W at a frequency of 2450 MHz;
   b. immersing Material A in 95% ethanol, wherein the ratio of Material A to ethanol (w/w) ranges from 1:5 to 1:15; irradiating the suspension with microwaves in a microwave extraction equipment with water condenser, wherein the overall microwave power is 1000W -1500W with the frequency of 2450 MHz, and wherein the suspension is exposed to microwave irradiation for 30-50min at a temperature of 45-65° C. while being stirred at 60-100 rpm; filtering the resulting extract at the pressure of 0.08MPa to permit evaporation of ethanol, thereby obtaining Material B; and
   c. drying Material B in a microwave-drying equipment at 50° C. and 0.08 MPa for 10-12 hours, wherein the overall microwave power is 1000W-1500W at the frequency of 2450 MHz, thereby obtaining crude solanesol.

* * * * *